United States Patent [19]

Bucalo

[11] 4,066,359
[45] Jan. 3, 1978

[54] METHOD AND STRUCTURE FOR TREATING BODY FLUIDS WITH CELLS THEREIN

[76] Inventor: Louis Bucalo, 155 Roberts St., Holbrook, N.Y. 11741

[21] Appl. No.: 688,728

[22] Filed: May 21, 1976

[51] Int. Cl.² .................. G01N 1/00; G01N 33/16
[52] U.S. Cl. ....................... 356/36; 73/61 R; 356/38; 356/39; 356/244; 356/246
[58] Field of Search ............ 356/36, 38, 244, 246, 356/39; 73/61.1 R, 61 R, 425.6

[56] References Cited

U.S. PATENT DOCUMENTS

| | | | |
|---|---|---|---|
| 3,063,289 | 11/1962 | Moul | 73/61 R |
| 3,940,250 | 2/1976 | Plakas et al. | 356/36 |

*Primary Examiner*—Vincent P. McGraw
*Attorney, Agent, or Firm*—Steinberg & Blake

[57] ABSTRACT

A method and structure capable of treating body fluids with cells therein for facilitating examination of cells. The body fluid sample is placed in a cylinder at one end of which is a filter, and then treating liquids are drawn into the cylinder through the filter while also being discharged out of the cylinder through the filter so that it is possible to carry out washing steps for washing out of the sample undesired components therein as well as placing in contact with the cells which are subsequently to be examined staining solutions, for example, so that a thorough staining is achieved. Thereafter the specimen remaining in the cylinder is placed on a slide and examined under a microscope. Preliminary to microscope examination, however, a barrier can be placed around the specimen on the slide and a solvent applied to the specimen held within the barrier so that undesired components which might obscure the vision, such as filaments or artifacts, can be dissolved out of the specimen, the barrier retaining the solvent in engagement with the specimen until the latter dries while the solvent evaporates, whereupon the specimen can be examined under a microscope.

12 Claims, 7 Drawing Figures

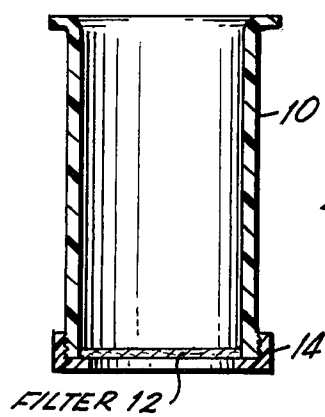
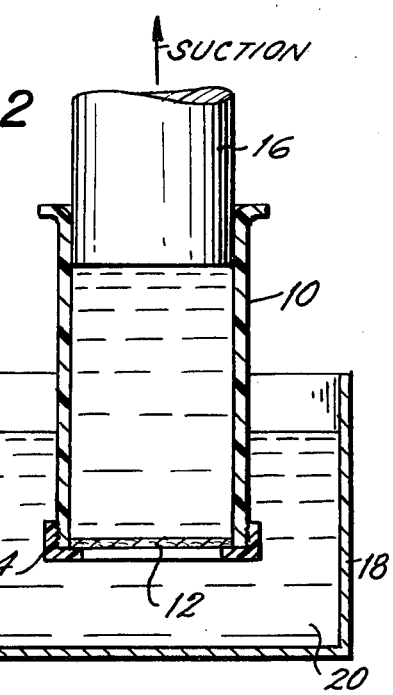
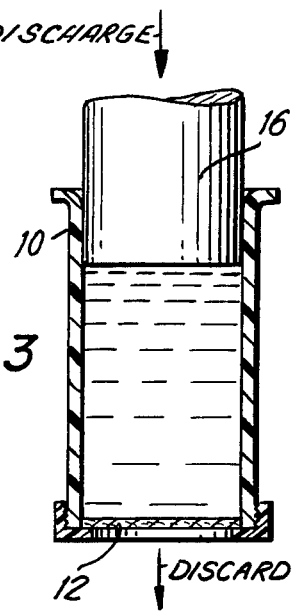
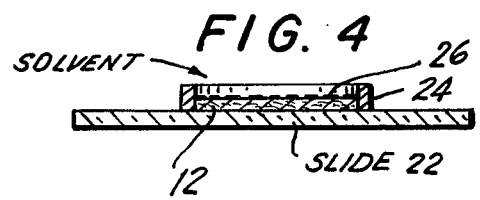
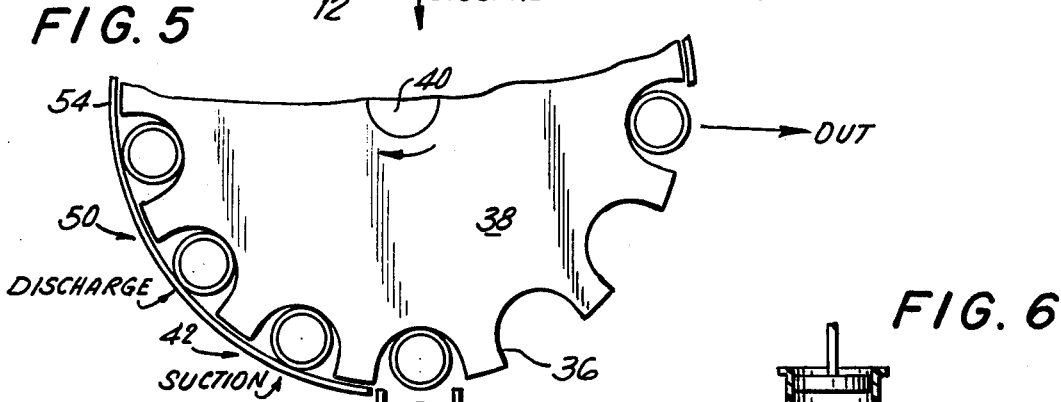
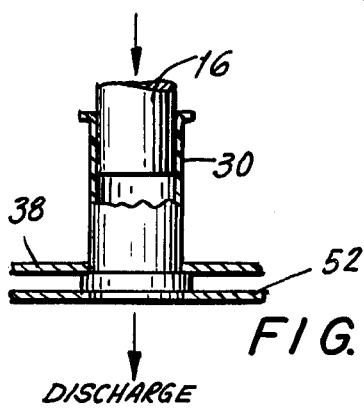
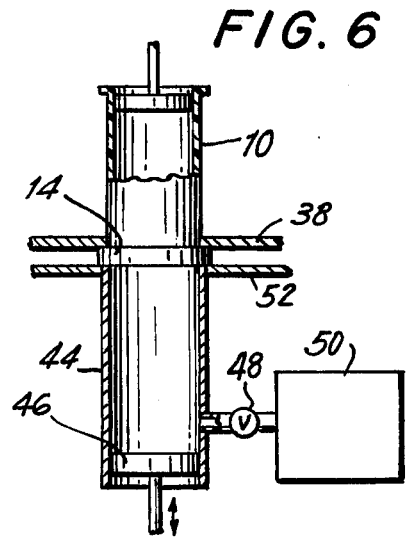

METHOD AND STRUCTURE FOR TREATING BODY FLUIDS WITH CELLS THEREIN

BACKGROUND OF THE INVENTION

The present invention relates to methods and apparatus for examining and analyzing cells, such as those encountered in body fluids of living beings, namely blood cells, tissue cells, bone marrow cells, and the like, as well as cells of microorganisms encountered in such body fluids, such as bacteria cells, fungi cells, or the like.

Normally such cells are collected by way of a swab or scraping technique, and the collected cells are then placed on a slide and dipped into various solutions. Then by way of a standard filtered technique such as the McCarty technique, the specimen is filtered and stained.

The above procedures involve several disadvantages. Thus the cells from one patient may be mixed with those of another patient. Also, the solution such as the staining solutions can reach each cell only from one direction inasmuch as the parts of the cells which are directed toward the slide cannot be reached by the solution and the slide itself is impervious to the solution. Thus, treatment is incomplete and slow, and it is easily possible for valuable cells to become lost during the various dippings into various solutions.

SUMMARY OF THE INVENTION

It is accordingly a primary object of the present invention to provide a method and apparatus which will avoid the above drawbacks.

In particular, it is an object of the present invention to provide a simple method and apparatus according to which it is easily possible to treat the cells which are to be subsequently examined in such a way that the treating solutions are capable of contacting the cells from all directions.

It is a further object of the present invention to provide a method and apparatus of the above type which lends itself either to simple inexpensive manual operation but which also lends itself to automatic techniques.

In addition it is an object of the present invention to provide a method and apparatus according to which various components can be used once and discarded, so that contamination of one specimen with another can be avoided.

In particular it is an object of the present invention to provide a method and apparatus according to which the possibility of undesirable washing away of valuable cells which are to be examined can be reliably avoided.

According to the invention a fluid sample taken from a body or from another source and having therein cells which are to be examined is placed in a cylinder which at its bottom end has a filter, and then apparatus cooperated with the cylinder for carrying out supply and discharge cycles. During the supply cycles it is possible to introduce into the cylinder liquids which will treat the sample initially placed therein, and during the discharge cycles the treating liquid is discharged through the filter. The treating liquid may be used for washing out of the sample undesired components as well as for treating the cells such as by staining them so that they will be more readily visible under a microscope.

BRIEF DESCRIPTION OF DRAWINGS

The invention is illustrated by way of example in the accompanying drawings which form part of this application and in which:

FIG. 1 is a sectional schematic elevation of a cylinder and filter assembly according to the invention;

FIG. 2 illustrates how the structure of FIG. 1 is associated with the plunger and then used to suck a solution into the cylinder through a filter thereof;

FIG. 3 shows a step subsequent to that of FIG. 2 during which the previously drawn in liquid is discharged;

FIG. 4 shows how the specimen is treated on a slide;

FIG. 5 is a fragmentary schematic elevation of an automatic treating apparatus;

FIG. 6 schematically illustrates how the structure of FIG. 5 operates at a suction station; and FIG. 7 illustrates how the structure of FIG. 5 operates at a discharge station.

DESCRIPTION OF PREFERRED EMBODIMENTS

Referring to FIG. 1, there is shown therein in a sectional elevation a cylinder 10 made of any inexpensive plastic and open at both of its ends, this cylinder carrying at its bottom end a filter 12. The filter 12 completely fills and extends across the interior of the cylinder 10 and engages the inner surface thereof with a substantial friction or is held in position by way of a suitable adhesive. However, the filter 12 is also retained in the cylinder by way of an internally threaded ring 14 which is threaded onto the lower end portion of the cylinder 10 in the manner shown in FIG. 1. As is schematically indicated in FIG. 1, a liquid sample taken from a body and having therein cells which are to be subsequently examined is introduced into the cylinder 10 in any suitable way. Thus, for example, known devices may collect fluid sampes in the interior of a body cavity and from these devices it is possible to discharge the sample into the cylinder 10 in the manner shown schematically in FIG. 1.

Thereafter, a plunger 16 is placed in the cylinder 10 in the manner shown schematically in FIG. 2, and the bottom end of the cylinder 10 is placed in a container 18 having therein a suitable treating liquid 20. During the suction stroke schematically shown in FIG. 2, the treating liquid is drawn through the filter 12 into the cylinder 10 so as to treat the specimen previously placed therein as shown in connection with FIG. 1.

After the treating liquid has thus been drawn into the cylinder 10, the latter together with the plunger 16 are displaced away from the container 18, and then the plunger 16 is displaced downwardly with respect to the cylinder 10, as shown schematically in FIG. 3, so as to displace the liquid out of the cylinder 10, and this displaced liquid which passes downwardly through the filter 12 in a manner shown in FIG. 3 can simply be discarded.

The above operations can be repeated with successive solutions. Thus, if cells are to be stained while they are still in solution, then the transfer of sequential solutions is more complete because the cells are capable of being impregnated from all directions. In the case of cells which are collected in a body fluid, such as vaginal or anal fluid or menses, the undesired mucous or debris can be filtered out by proper selection of filters and washing liquids. Thus a suitable agent which will break down mucous can be used, and repeated washings of the filter similar to backwashing can be utilized to remove debris and undesired components.

The sequential treatment with liquids for staining purposes can take place according to the sequential steps of the "Pap" procedure, before the cells are fixed on a slide or on the filter surface. Each solution is backwashed into the chamber of the cylinder and then discarded through the filter and drained.

The residue which remains on the filter can then be placed therewith on a slide 22 as schematically shown in FIG. 4. Thus, the ring 14 can be unthreaded and the filter 12 with the residue thereon can be removed from the cylinder 10 and transferred onto the slide 22. According to a further feature of the invention, a suitable barrier in the form of a ring 24 is placed on the slide around the specimen 26 which has been placed on the slide in the manner described above. This ring 24 can have any desired shape. For example, it can be round, square, rectangular, the only requirement being that it be capable of forming a seal with the surface of the slide while having an open top. Through this open top a suitable solvent is introduced as schematically indicated in FIG. 4. A solvent for the filter material, e.g. chloroform for a polycarbonate filter, is introduced and can be of the type which forms a hard plastic in which the specimens are embedded and in which they are easily visible, and the solvent can be used to dissolve filamentary material such as filaments or artifacts from the filter or from other undesired sources. Thus, such filamentary material or artifacts remaining in the specimen are disturbing to the eye under a microscope and make it difficult to evaluate the specimen. The barrier 24 will retain the solution which hardens to contain the cells therein while dissolving the filaments and the like, and after the specimen 26 treated in this way has dried, the specimen is readily examined under a microscope in a manner which is far more effective than has heretofore been possible.

While the method and apparatus described above are particularly suited for manual operation, it is also possible to carry out the operations automatically in a manner schematically in FIG. 5. Thus FIG. 5 shows a series of units 30 corresponding to a cylinder with a filter at its bottom, a specimen therein and a plunger thereon, the several units being guided by a pair of guides 32 and fed step by step, as shown by the arrow 34 into successive pockets 36 of a rotary transporting plate 38 driven in a step-by-step manner by a suitable manner 40. Thus, the means 34 can take the form simply of a plunger guided between the guides 32 and urged by a spring toward the motor 40. Thus, as each pocket 36 moves past the gides 32 another unit 30 will be received in a pocket 36. The several stations to which the units 30 are transported in a step-by-step manner are several suction and discharge stations where the steps described above in connection with FIGS. 2 and 3 take place are are repeated as many times as desired. Thus, at the suction station 42, it is possible, as shown in FIG. 6, to have a container 44 which is closed at its bottom by a reciprocating piston 46 actuated by way of a suitable timed mechanism such as a crank which is driven in a proper time sequence. At every downward stroke of the piston 46 the treating solution can be drawn into the container 44 through a one-way valve 48 from a source 50. During the upward stroke the solution in the container 44 is pushed into a cylinder 10 through the filter thereof. It will be noted that the table 38 engages each cylinder 10 just above the ring 14 so that the cylinder 10 will remain at the position shown in FIG. 6 while a treating liquid is introduced into the same.

During the next step the cylinder 10 is displaced from the position of FIG. 6 to that of FIG. 7 corresponding to a discharge station 50. At this discharge station the bottom end of the cylinder 10 is simply supported on a table 52 over which the specimens are moved in a slidable manner during the rotary movement of the transporting plate 38, a suitable ring 54 surrounding the transporting plate and being situated on the table 52 to retain the several units 30 in the several pockets. At each discharge station the table 52 is formed with an opening which becomes aligned with the unit 30, and at each discharge station there is situated over the plunger 16 a suitable rotary cam or the like which acts on the plunger to move it downwardly in order to discharge the liquid out of the cylinder, this discharge liquid simply being received in any suitable drain and discarded.

In the above manner the several washings or the like can be successively carried out in an automatic way.

The filter which is used will of course be made of different materials or different porosities depending upon the sample which is to be treated and the treatment which is desired. In general, however, the filter can be made of polycarbonate and can have relatively fine pores.

As has already been indicated above, the cells which are to be analyzed according to the method and apparatus of the invention are of the type which are encountered in a body fluid, such as blood cells, tissue cells, or the like, or cells of microorganisms such as bacteria, fungi, or the like.

Moreover, instead of examining the cells under a microscope, it is also possible to place the specimen formed by the residue remaining on the filter in a suitable solution which with the cells therein can be placed in a colorimeter tube so that in a suitable colorimeter instrument light of a given wavelength can be directed through the solution with the cells therein to obtain the desired information with respect thereto. Thus, in this latter connection it is possible to the last operation to be the drawing into the cylinder of the solution in which the cells are to be situated when examined in the colorimeter, and then this solution with the cells therein can be poured into a colorimeter sample tube and thus be examined in the colorimeter.

Moreover, with an automatic arrangement as shown in FIGS. 5–7 it is not essential to use precisely the structure illustrated. For example instead of providing cams or the like to act on the plungers which are in the cylinders, these plungers can be eliminated and instead the cylinders can be successively brought into line with suitable sources of suction and pressure which act through the top open ends of the cylinders to draw treating fluids into the cylinders through the filters when the interiors of the cylinders are placed in this way with a source of suction, while when the cylinders are placed in communication with a source of pressure the liquid previously drawn in during communication with a source of suction can be discharged. Moreover, it is also possible to operate automatically only with suction alternately applied to the top and bottom of each cylinder as it travels from one station to the next. Thus when suction is applied to the top end of the cylinder a treating fluid can be drawn into the cylinder through the filter, while when suction is applied to the cylinder through the bottom end thereof, the liquid previously drawn in can be drawn down through the filter and then discarded. Also it is possible to operate only with pressure, utilizing for exxample a gas such as air at a suitable pressure and applied successively to the top and bottom of the cylinder for carrying out discharge and introduction of treating liquids, respectively. If desired the treating liquids can simply be poured into the cylinder through the open top thereof and then discharged either by pressure applied to the top or suction applied to the bottom of the cylinder. Thus, by way of any of the above procedures it is possible to carry out successive supply and discharge cycles during which treating liquids are each respectively supplied to the interior of the cylinder and discharged out through the filter.

What is claimed is:

1. In a method for preparing for subsequent analysis cells of the type encountered in the body of a living being, such as tissue cells, blood cells, marrow cells and the like or cells of microorganisms such as bacteria, fungi, or the like, the steps of placing in a cylinder carrying a filter a sample in the form of a fluid which has therein cells which are to be analyzed, then carrying out supply and discharge cycles with respect to the interior of the cylinder and while carrying out a supply cycle directing into the interior of the cylinder a treating liquid which when entering the cylinder contacts the sample for at least partly contributing toward placing the cells which are to be subsequently analyzed in a given condition, and while carrying out a discharge cycle discharging the treating liquid through the filter out of the cylinder while also discharging with the treating liquid undesired components from the sample.

2. In a method as recited in claim 1 and wherein the supply and discharge cycles are repeatedly carried out with a plurality of different treating liquids.

3. In a method as recited in claim 2 and wherein the treating liquids are washing liquids for eliminating from the sample undesired components which wash out through the filter during the discharge cycles.

4. In a method as recited in claim 2 and wherein the different treating liquids include identifying solutions for giving to the cells a condition which will render them identifiable when subsequently analyzed.

5. In a method as recited in claim 4 and wherein the different treating liquids include at least one staining solution, and including the step of removing from the cylinder the filter and residue remaining thereon after staining and forming a specimen which is to be examined, placing the filter with the specimen thereon on a slide, and examining the specimen on the slide under a microscope.

6. In a method as recited in claim 4 and including the step of situating the cells which are to be analzyed in a solution which with the cells therein which are to be analyzed can be examined by directing through the solution with the cells therein light of a given wavelength.

7. In a method as recited in claim 5 and including the step of placing, before examination of the specimen under a microscope, while the specimen is on a slide, a barrier around the specimen and filter carrying the specimen, and adding to the specimen a solvent which will dissolve therefrom components such as filaments or other artifacts and the like which might detract from the visibility of the cells under the microscope, said barrier preventing the solvent from flowing undesirably away from the specimen on the slide.

8. In a method as recited in claim 4 and including the step of automatically carrying out the various steps in connection with repeated supply and discharge cycles and repeated contacting of the sample with different treating liquids.

9. In a method as recited in claim 4 and wherein the body fluid is menses fluid.

10. In a device for treating a body fluid sample containing cells which are to be analyzed, a cylinder carrying at one end a filter, so that the fluid sample can be placed in the cylinder, and means cooperating with said cylinder for carrying out supply and discharge cycles with various treating liquids in such a way that during a supply cycle a treating liquid can be introduced into the cylinder to treat a sample previously placed therein while during the discharge cycles the treating liquid previously introduced during the supply cycles can be discharged through the filter.

11. The combination of claim 10 and wherein at least said cylinder and filter are made of inexpensive materials so that they can be discarded after use.

12. Apparatus for automatically treating samples of body fluids with cells therein, with the samples respectively situated in cylinders which have filters at their bottom ends, transporting means for transporting the cylinders with the samples therein one after the other to a series of stations, means at some of said stations for cooperating with the cylinders to introduce into the interior thereof treating liquids for treating the sample initially situated therein, and means at other stations for discharging the treating liquid out of the cylinders through the filters thereof, so that after the cylinders have been transported to the several stations the cylinders can be removed and specimens remaining therein can be examined.

* * * * *